United States Patent [19]

Drezner et al.

[11] Patent Number: 5,019,401

[45] Date of Patent: May 28, 1991

[54] ALUMINUM SALTS IN THE TREATMENT OF BONE DISEASE

[75] Inventors: Marc K. Drezner; L. Darryl Quarles, both of Durham, N.C.

[73] Assignee: Duke University, Durham, N.C.

[21] Appl. No.: 364,590

[22] Filed: Jun. 12, 1989

Related U.S. Application Data

[63] Continuation of Ser. No. 913,398, Sep. 30, 1986, abandoned.

[51] Int. Cl.$^5$ .............................................. A61K 33/14
[52] U.S. Cl. ..................................... 424/662; 424/682
[58] Field of Search ................................ 424/662, 682

[56] References Cited

U.S. PATENT DOCUMENTS

| | | | |
|---|---|---|---|
| 2,827,420 | 3/1958 | Wiershaw | 424/154 X |
| 4,146,605 | 3/1979 | Ritchey | 424/154 X |
| 4,260,597 | 4/1981 | Porteous | 424/154 X |
| 4,556,564 | 12/1985 | Laurent et al. | 426/2 |

OTHER PUBLICATIONS

The merck Index, 9th ed., 1976, pp. 44-49.
"Aluminum Deposition at the Osteoid-Bone Interface", L. D. Quarles, et. al., *Journal of Clin. Invest*, vol. 75, May 1985, 1441-1447.
"Aluminum: Culprit or Accessory in the Genesis of Renal Osteodystrophy", L. D. Quarles, et al., Seminars in Nephrology, vol. 6, No. 1 (Mar.), 1986: pp. 90-101.
"Presenting Ethacal TM Feed Component" Brochure; Ethyl Chemicals Group.

*Primary Examiner*—Leonard Schenkman
*Attorney, Agent, or Firm*—Oblon, Spivak, McClelland, Maier & Neustadt

[57] ABSTRACT

A method for stimulating the formation of new mammalian bone, which entails administering an effective amount of one or more water-soluble aluminum salts to a mammal.

8 Claims, 5 Drawing Sheets

ALUMINUM SALTS IN THE TREATMENT OF BONE DISEASE

This application is a continuation of application Ser. No. 06/913, filed on Sept. 30, 1986, now abandoned.

BACKGROUND OF THE INVENTION

1. Field of the Invention

The present invention relates to the use of aluminum salts in the treatment of bone disease.

2. Description of the Background

Bone is a dynamic tissue which constantly remodels itself throughout life. The properties of this tissue are a function of the particular organization of its extracellular components. The structure of bone tissue consists of a solid mineral phase in close association with an organic matrix consisting of 90–95% collagen, small amounts of proteoglycans and some non-collagenous proteins including proteins containing a-carboxyglutamic acid. The mineral phase is composed of hydroxyapetite, having the empirical formula $Ca_{10}(PO_4)_6(OH)_2$, of small crystal size and poor crystallinity, and so-called "amorphous" calcium phosphate, having a lower molar calcium/phosphorus ratio than that of hydroxyapetite.

The mineral phase of bone is deposited in intimate relation to the collagen fibrils and is found, for the most part, in specific locations within the collagen fibrils. The architectural organization of the mineral and matrix phases are uniquely suited to withstand mechanical stresses. In fact, the skeleton has extraordinary mechanical functions well-suited to the needs of mobile vertebrates. For example, the particular arrangement of compact and cancellous bone provides an excellent combination of bone strength and density for these needs. Additionally, bone provides a store of calcium, magnesium, phosphorus, sodium and other ions necessary for the support of a variety of homeostatic functions.

Bone is formed by cells of mesenchymal origin which synthesize and secrete the organic collagenous matrix. Mineralization of the matrix appears to commence soon after secretion, but is usually not completed until after several weeks. Osteoblasts synthesize and secrete the matrix, which is then mineralized. These cells once surrounded by the matrix become osteocytes, which remain connected to the blood supply through a series of canaliculi.

In the embryo and in the growing child, bone develops either by primary modeling and replacing of previously calcified cartilage, i.e., endochondral bone formation, or it is formed without a cartilage matrix, i.e., intramembranous bone formation. The young new bone has a relatively high ratio of cells to matrix and is characterized by coarse fiber bundles of collagen which are interlaced and randomly dispersed. In adults, the more mature bone is organized with fiber bundles regularly arranged in parallel or concentric sheets.

Growth of bone in width and in thickness is accomplished by the formation of bone at the periosteal surface and resorption at the endosteal surface with the rate of formation exceeding that of resorption. As noted above, however, bone remodeling, even in adults, is a continuous process occuring throughout life. In fact, kinetic studies using isotopes such as radioactive calcium ($^{47}Ca$) provide estimates that as much as 18% of the total skeletal calcium may be deposited and removed each year. Moreover, it appears that this constant bone remodeling is effected in a manner related to the continuous mechanical stresses to which the bone is subjected.

Bone formation is an orderly process in which inorganic materials such as calcium and phosphorus are desposited in a collagenous matrix. As the mineral phase is composed largely of calcium and phosphorus, the concentration of these ions in the blood plasma and extracellular fluid influences the rate of mineral phase formation. However, the concentration of these ions at the sites of mineralization is unknown and it is possible that osteoblasts and osteocytes may be involved in regulating the local concentration of these and other ions.

Nevertheless, there appears to be a lower limit for the concentration of calcium and phosphorus in the extracellular fluid below which the mineral phase will not be formed. Conversely, when these concentrations are excessive, the formation of mineral phases is observed in areas that are not normally mineralized.

During the resorption of bone, calcium and phosphorus ions from the solid phase are released into solution in the extracellular fluid, and subsequently, the organic matrix is also resorbed. Although the resorption mechanism is not entirely clear, it has been postulated that a decrease in pH, the presence of one or more chelating agents or the operation of a cellular pump mechanism to shift the equilibrium between solids and solution may be involved.

A number of diseases in man are characterized by diminished bone volume. Osteoporosis is the term used to describe the group of diseases of diverse etiology which are characterized by a reduction in the mass of bone per unit volume to a level below that required for adequate mechanical support. Histologically, osteoporosis is characterized by a decrease in the number and size of the trabeculae of cancellous bone with normal width of the osteoid seams.

Any combination of changes in the rates of formation and resorption which results in an excess of bone resorption relative to formation can cause a decrease in bone mass. In osteoporosis the bone mass is decreased, indicating that the rate of bone resorption must exceed that of bone formation.

Resorption and formation of bone are normally tightly coupled processes. However, the rate of remodeling is not uniform throughout the skeleton after epiphyseal closure. In fact, some of the bone surfaces are "inactive" and not involved at any given time either in formation or resorption. Resorption areas are covered by osteoclasts if active, whereas bone formation surfaces are characterized by the presence of osteoid seams and are covered by active osteoblasts. Thus, while the active surfaces may be randomly distributed, formation and resorption are coupled as so-called "remodeling units."

After the age of about 35 to 40 years, the human skeletal mass begins to decline in different parts of the skeleton. Evidence obtained from kinetic studies, using radioactive isotopes of calcium and phosphorus, and from quantitative microradiography, of both cortical and cancellous or trabecular bone indicates that in most subjects the resorption rate is higher than normal, whereas the bone formation rate is somewhat lower. Radioactive calcium kinetics indicate that as much as 400 to 500 mg of calcium may enter and leave the normal adult skeleton daily. At some critical point, if the difference between rates of formation and resorption is maintained, loss of bone substance may become so pronounced that the bone can no longer resist the mechanical forces to which it is subjected, and fracture occurs. Osteoporosis would then be presented as a clinical problem. Unfortunately, the cause of this age-associated decrease in bone mass and increase in bone resorption, which occurs particularly in older women after menopause, is not known. However, it has been estimated that, at present, approximately 50 million perimenopausal and postmenopausal women are afflicted with this condition.

Presently, all attempts to treat this disorder are prophylactic in nature. For example, medicinal agents commonly employed such as supplements of calcium, estrogens, vitamin D, and calcitonin are designed to inhibit bone resorption, and thereby merely retard the natural evolution of bone loss which occurs with aging. While such treatments are of some use, they suffer from two serious disadvantages. First, the success of these treatments depends, to a critical extent, upon the early identification of at-risk subjects before irreversibly damaging bone loss has occured. Secondly, even if such early identification is achieved, the success is limited in that all that is accomplished is a slowing of a seemingly inevitable and naturally occuring process. Thus, with the U.S. population living to an older age, we are, in essence, only succeeding in delaying the still inevitable onset of osteoporosis.

Although several drugs which are presently in investigational stages appear to have some capability of increasing bone volume, each has serious drawbacks which limit the utility thereof. For example, the application of fluoride ions in chronic high doses appears to increase new bone formation. However, these high doses tend to produce a form of hyperostosis with dense bones, exostoses, neurological complications due to bony overgrowth, and ligamentous calcification. Also, the administration of fluoride ions is often associated with the appearance of ulcers, arthritides and osteomalacia, wherein there is defective mineralization of the newly formed organic skeletal matrix. Furthermore, the use of fluoride in treating osteoporosis has not been found to produce uniformly satisfactory results, possibly due to variations in dosage, retention of absorbed ion and concurrent calcium intake.

Parathyroid hormone (PTH) has been observed to increase trabecular bone volume to some extent, however, only at the expense of cortical bone. In essence, administration of parathyroid hormone robs cortical bone in order to build trabecular bone. Cortical bone is characterized by having canals therethrough for blood passage. By contrast, trabecular bone is characterized by having islands of bone immersed in the marrow, and, therefore, has a large surface area. Inasmuch as metabolic changes in bone occur mainly on the bone surfaces, bones with high surface areas are the most susceptible to formation and resorption cycles.

While some bones, such as the more compact bones, are about 90% trabecular bone, other bones, such as the wrist bones are about 90% cortical bone. Hence, forming trabecular bone at the expense of cortical bone is a serious disadvantage when administering parathyroid hormone.

In some cases of severe bone fracture or destruction by disease, various artificial devices such as metal plates have also been used to effect internal bone fixation. Typically, a metal plate is placed on the bone to bridge the fracture and afford rigidity and strength during healing. Such plates are normally made from cobalt, titanium alloys or stainless steel. Unfortunately, the desired purpose of bone formation may be defeated by resorption of the bone when insufficient stress is placed on the bone. Moreover, most metals readily undergo fatigue fracture in physiological environments if the bone does not heal. While some advances have been made with polymeric plates, polymeric materials often result in the necrosis of nearby tissues due to residual monomer.

Clearly, in view of the above, there are no therapies currently available for inducing bone formation. While there are therapies and techniques for diminishing bone resorption, all of these methods suffer from severe drawbacks. Additionally, even the use of artificial mechanical supports, such as metal or polymeric plates, is greatly hampered by side effects or inherent limitations.

Accordingly, a need continues to exist for a method for stimulating the formation of new bone. Further, it would be very desirable if a method for stimulating new bone formation could be attained which uncouples the formation process from the resorption process which is normally coupled thereto.

SUMMARY OF THE INVENTION

Accordingly, it is an object of the present invention to provide a method for stimulating the formation of new bone.

It is also an object of this invention to provide a method for stimulating the formation of new bone without causing concurrent bone resorption.

Moreover, it is also an object of this invention to provide pharmaceutical compositions for effecting the above-described new bone formation.

According to the present invention, the foregoing and other objects are attained by providing a method for stimulating the formation of new mammalian bone, which entails administering an effective amount of one or more water-soluble aluminum salts to a mammal.

BRIEF DESCRIPTION OF THE DRAWINGS

At the outset, it is noted that beagles were selected as appropriate animal models for investigation given the recognition in the art that dogs are the best and most reliable animal models for conducting bone studies which approximate the human bone system. For example, it is known that canine bones experience both resorption and reformation, whereas the bones of the rat, by contrast, experience only formation.

DETAILED DESCRIPTION OF THE PREFERRED EMBODIMENTS

Figure 1B:
FIG. 1b illustrates a Villanueva-stained bone section viewed under polarized light. In this illustration, the same section presented in FIG. 1a, is examined for the presence of lamellar bone formation. Under polarized light the lamellar nature of the trabeculum and the buds of new bone formation are evident. Thus, the burst of new bone formation occurring in response to the low dose aluminum administration results in production of normally mineralized and structured bone.
Figure 1A:
FIG. 1a illustrates a Villanueva-stained bone section from a beagle treated 16 weeks with low-dose aluminum chloride (0.75 mg/kg) administered intravenously 3 times per week. Immediately apparent is a marked degree of active bone formation resulting in budding of new bone at the trabecular surface. The apparent budding is in marked contrast to traditional bone formation which occurs within previously etched Howship's lacunae. Moreover, the osteoid covered bone surfaces over the buds have abundant osteoblasts on the perimeter.
Figure 2B:
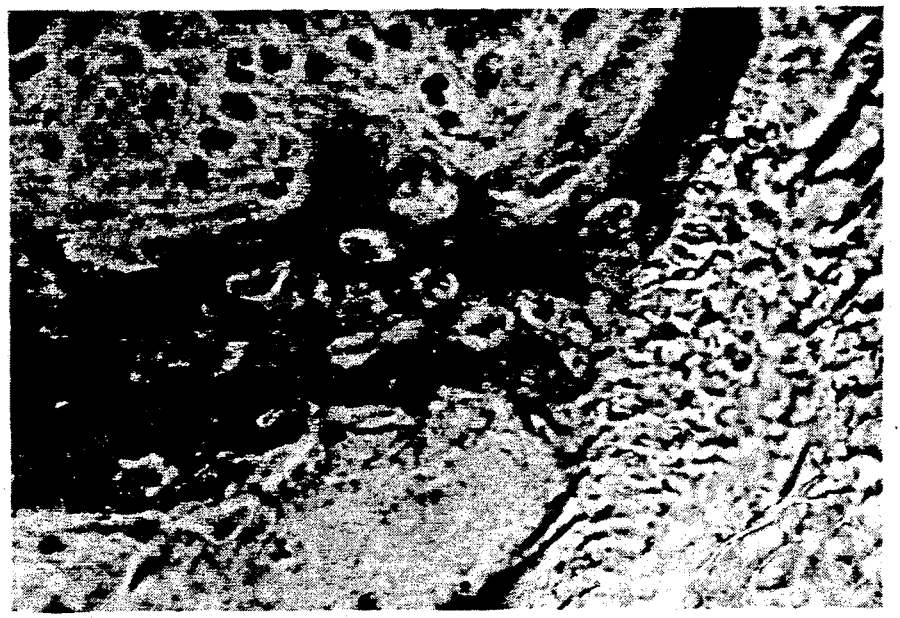
FIG. 2b illustrates a high power view of the fibrous bone desposited in response to high-dose aluminum therapy. This section, stained by the methods of Villanueva, reveals that within the fibrous tissue (deep blue tones) a large number of plump osteoblasts apparently functioning at high levels of activity are present.
Figure 2A:
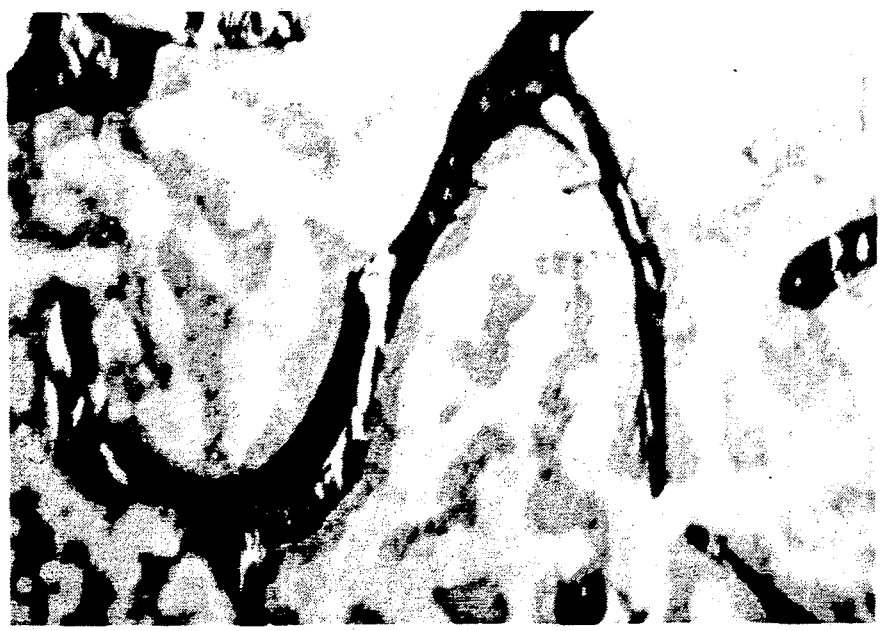
FIG. 2a illustrates a Goldner-stained bone section viewed under low power light microscopy from a beagle treated with high-dose aluminum (1.25 mg/kg) three times weekly intravenously for eight weeks. Immediately evident is a abundance of new bone in the form of unmineralized fibrous bone (the tan-brown toned materials). Some of this new bone is juxtaposed to previously existing trabeculae while other new bone is apparently free in the marrow cavity. The presence of fibrous bone is indicative of increased numbers of osteoblasts functioning at high levels of activity, consistent with marked stimulation of new bone formation.
Figure 3B:
FIG. 3b illustrates the same section viewed under polarized light. This illustration demonstrates that the calcified trabecular bone is lamellar in nature while the apparent fibrous bone is indeed woven, establishing its unique nature.
Figure 3A:
FIG. 3a illustrates a Goldner-stained bone section viewed under high-power light microscopy from a dog treated 8 weeks with high-dose aluminum chloride (1.25 mg/kg) 3 times weekly intravenously. The brown toned material lining the trabecular surfaces represents fibrous bone, the result of the increased osteoblast number and activity.
Figure 4B:
FIG. 4b illustrates the same section viewed under polarized light. This illustration identifies that the previously existent trabecular bone is composed of lamellar collagen. In contrast, the newly mineralized tissue at the center of the picture is mineralized fibrous bone. This establishes that the woven bone formed in response to aluminum therapy at high doses, initially unmineralized, can be completely calcified upon cessation of aluminum therapy, resulting in substantial increases in trabecular bone volume.
Figure 4A:
FIG. 4a illustrates a Villanueva-stained bone section viewed under high power light microscopy from a beagle treated 8 weeks with high-dose aluminum chloride (1.25 mg/kg) 3 times weekly intravenously and subjected to 10 weeks off all therapy prior to bone biopsy. Compared to FIG. 2a, there is a much lesser amount of unmineralized woven bone. This has been replaced in great measure by mineralized bone tissue, thus increasing the mineralized bone volume substantially. The mineralized tissue is represented by the off-white tones and the unmineralized tissue by the blue-colored areas.
Figure 5B:
FIG. 5b illustrates the same section viewed under polarized light. This figure illustrates that the arborized portion of the bone tissue represents calcified woven bone which was formed and mineralized during continuous aluminum administration at 16 weeks of therapy.
Figure 5A:
FIG. 5a illustrates a Villanueva-stained bone section viewed under high power light microscopy from a beagle treated for 16 weeks with intermediate dose aluminum chloride (1 mg/kg) administered 3 times per week intravenously. The white-toned bone is present in abundance and has an arborized pattern of architecture with a smaller trabeculum emanating from the older present at the bottom of the figure. The newly formed tissue is rather completely mineralized but apparently represents fibrous bone that has successfully calcified. This mineralization has occurred in spite of continuous aluminum chloride therapy. Additionally, of import is the relative absence of unmineralized fibrous tissue.

According to the present invention, a means is now provided for stimulating new bone formation. In particular, it has now been found that the administration of water-soluble aluminum salts to mammals in effective amounts results in the stimulation of new mammalian bone formation.

In part, the present invention is based upon the discovery that the administration of one or more of the water-soluble aluminum salts to a mammal results in a marked proliferation of osteoblasts, which are the cells responsible for the synthesis and secretion of collagen, the organic bone matrix. The increased activity as evidenced by the formation of so-called fibrous bone, which by its presence alone is indicative of enhanced osteoblastic function A remarkable aspect of this increased new bone formation is its occurence with a concomitant decrease in bone resorption activity. As noted previously, bone turnover, i.e., resorption- and formation, is a tightly coupled process. The initiating event is bone resorption effected by osteoclasts and the final event is the replacement of resorbed bone by osteoblastic activity and mineralization. In effect, the water-soluble aluminum salts of the present invention not only increase osteoblast activity, but also appear to uncouple bone formation from the generally accepted prerequisite, bone resorption. It is this property or aspect of the present invention which is most important in order to effectively treat a number of diseases characterized by decreased trabecular and cortical bone volume. Thus, the water-soluble aluminum salts of the present invention can be used effectively in the formation of new bone no matter how severe the existent osteopenia. That is, the effects of the present salts appear to be independent of the antecedent trabecular bone surfaces.

Generally, after initial bone formation, the new bone is remodeled. In more detail, new mineralized woven bone is remodeled and replaced by mineralized lamellar bone. The woven bone merely comprises collagen fibers in discord. This disarray is, of course, due to the fact that the osteoblasts secrete collagen in every direction. However, in time, lamellar bone is formed, which entails an ordered array of collagen fibers, which are cross-linked at specific points. Thus, the lamellar bone matrix appears to be a more stable, more ordered matrix.

In particular, the water-soluble aluminum salts of the present invention, when administered, stimulate the formation of new woven bone, which, in turn, is remodeled, as described above, to lamellar bone. Moreover, the stimulation of new trabecular and cortical bone is observed.

According to the present invention, the term "water-soluble aluminum salts" encompasses all salts of aluminum which are sufficiently water-soluble. Of course, it is preferred if these salts also have, at least, some ionic character.

For example, the following salts may be used in accordance with the present invention: aluminum acetate, aluminum bromate, aluminum bromide, and hexa- and pentadecyl hydrates thereof, aluminum chlorate, aluminum citrate, aluminum chloride and the hexahydrate thereof, aluminum fluoride, aluminum iodide and the hexahydrate thereof, aluminum lactate, aluminum nitrate, aluminum sulfate and the hydrate thereof. However, of these the salts of aluminum chloride, bromide, fluoride, iodide, nitrate, sulfate, citrate and lactate are preferred. However, especially preferred are the salts aluminum chloride, fluoride and citrate.

In general, the salts of the present invention are conveniently added to water to form an aqueous solution of the same, and then the aqueous solution of the salt or salts is administered to a mammal. Generally, in order to obtain a sufficient amount of new bone formation, a dosage level in the range of 0.05-5.0 mg/kg of body weight is administered 1 or more times weekly until the desired effect is obtained. More preferably, the dosage level is in the range of 0.25-1.25 mg/kg administered 2-4 times weekly. Even more preferably, the dosage level is in the range of 0.25-1.25 mg/kg administered 3 times weekly. More preferable still, the dosage level used is in the range of 0.75-1.00 mg/kg administered 2-4 times weekly, usually 3 times weekly.

The recited dosage levels are administered for a time sufficient to produce the desired formation of new bone. In general, the therapy may last for as little as 1 or 2 weeks, or as long as several years, if necessary. However, as a practical matter, the administration will take place over a period of about 4 weeks or 1 month up to and including about 16 weeks or 4 months. Most preferably, the administration will take place over a period of about 8 weeks or 2 months up to and including about 16 weeks or 4 months.

For ease of administration, it is convenient to prepare aqueous solutions of about 0.1-20% by weight in concentration, which can then be administered intravenously. Although the salts of the present invention can be administered orally either as dry powders or tablets or in solution form, it is preferred that they be administered intravenously.

Suitable dry formulations can be made containing from about 10 mg to 500 mg of the aluminum salt or salts per unit dose. The unit dosage or portions thereof can then be consumed in accordance with the prescribed dosage level. For example, a 200 lb. human male, i.e., 90.9 kg., might be prescribed 1 mg/kg, 3 days per week. Thus, he would need for each administration, about 91 mg of aluminum salt. This amount could be ingested neat or with a suitable non-toxic pharmaceutical excipient. Examples of such excipients are various consummable substances such as candies, pleasant-flavored powders or chewable gums which release the aluminum salt or salts as chewed. In processing such substances, one or more aluminum salts of the present invention could merely be adding to existing and well-known formulations.

However, as noted, the preferred means of administration is intravenously. Hence, for a solution which is 0.5% by weight of aluminum salt, and using the same 200 lb. human male model, an injection of about 20 ml would be required per administration.

Of course, the aluminum salts, themselves, of the present invention can be obtained from a variety of sources. For example, see the Aldrich Catalogue of Chemicals (1986).

Generally, the method of the present invention can be used with any mammalian host, such as dogs, cats or other animals. However, the present method is deemed to be particularly advantageous in the treatment of human bone diseases.

The present invention will now be further illustrated by the following Examples which are provided for purposes of illustration only and are not intended to limit the present invention.

EXAMPLES

Study Protocol

Beagle puppies of variable weight, i.e., from about 10 to 15 kg. were randomly divided into 4 groups. Group 1, a control group, received a normal diet containing about 0.7% calcium, 0.5% phosphorus and 2,200 $\mu$/kg vitamin $D_3$. By contrast, Groups 2, 3 and 4 receiving progressively increasing doses of aluminum chloride in aqueous solution, administered intravenously thrice weekly.

The dogs of Group 2, numbered 16, 3, 17, 15 and 122 received a low dose of 0.75 mg/kg (LDA) thrice weekly, and were assayed at intervals of 8 and 16 weeks. The dogs of Group 3, numbered 116, 121, 123 and 8941 received an intermediate dose of 1.00 mg/kg (IDA) thrice weekly, and were assayed at intervals of 8 and 16 weeks. Finally, the dogs of Group 4, numbered 5, 18, 14 and 20 received a high dose of 1.25 mg/kg (HDA) thrice weekly, and were assayed only at 16 weeks.

Biochemical Studies

Plasma calcium, phosphorus creatinine and alkaline phosphatase were measured by colorimetric techniques using an autoanalyzer (Technicon Instruments Corp., Tarrytown, N.Y.).

The plasma parathyroid hormone (PTH) concentration was measured using a radioimmunoassay kit (Nichols Laboratories, Inc.) designed to measure the N-terminal portion of the molecule according to the known method of Potts et al, see *Radioisotopes in Medicine*, U.S. Atomic Energy Commission "RIA of PTH: Studies of the Control of Secretion of the Hormone and Parathyroid Function in Clinical Disorders" (1968).

The plasma 25-hydroxyvitamin D (25(OH)D) concentration was measured by a modification of the known method of Haddad and Chyu, see *J. Clin. Endocrinol*, 33:992-995 (1971).

The ionized calcium level was determined using an ICAI analyzer (Radiometer Co., Copenhagen, Denmark), and values were corrected to a pH of 7.4.

Plasma aluminum concentrations were assayed according to the known method of Alderman et al, see *Clin. Chem.* 26: 258-260 (1980), using a flameless atomic absorption spectrophotometer (Perkin-Elmer Corp., Instrument Div., Norwalk, Conn.) with a graphite furnace. Interference was minimized by using a diluent containing ammonium hydroxide. The average plasma aluminum level was estimated by measuring the plasma concentration at variable intervals for 48-72 hours after an intravenous injection and determining the area under the plasma concentration versus time curve, using the trapezoidal rule, divided by the interval between doses.

Bone studies. Transcortical bone biopsies were obtained from the anterior iliac crest of dogs under general anesthesia. Chlortetracycline (250 mg orally, twice daily) was administered to each dog over a 3-d period from day 21 to day 18 before biopsy and calcein (15 mg/kg by IV, one time) from day 6 to day 3 before biopsy. Bone specimens were fixed in ethanol and embedded in methylmethacrylate, unstained or prestained by the known methods of Villanueva. 20- and 5-$\mu$m prestained and unstained sections by a modification of known methods reported by Maloney et al.

Histomorphometric analysis of both static and dynamic parameters of trabecular bone remodeling were performed in each section using a semi-automated system (Osteoplan; Zeis, West Germany). Supplemental analysis was performed with an integrated reticle (Merz-Schenk; Eild, Heerbrugg, Switzerland) for certain parameters. The following histologic functions were quantitated:

1. Bone volume (VV), the area of trabecular bone per tissue volume.
2. Surface density of bone (SV), the surface of trabecular bone per tissue volume.
3. Trabecular diameter (D-TRAB), the average width of trabeculae.
4. Woven bone volume (VV-w), the area of woven bone per tissue volume.
5. Osteoid volume (VV-OS), the osteoid area per tissue volume.
6. Surface density of osteoid (SV-OS), the surface of osteoid-covered trabecular bone per tissue volume.
7. Osteoid surface (OS), the surface of osteoid per surface of trabecular bone.
8. Relative osteoid volume (ROV), the osteoid area per trabecular bone volume.
9. Mean osteoid seam width (MOSW), the mean width of osteoid seams.
10. Woven osteoid volume (VV-OS-W), the woven osteoid area per trabecular bone volume.
11. Woven osteoid surface (OS-W), woven osteoid-covered trabecular bone surface per surface of trabecular bone.
12. Relative woven osteoid volume (ROV-W), the woven osteoid area per trabecular bone volume.
13. Thickness of woven osteoid (TH-OS-W), the mean width of woven osteoid on trabecular bone surfaces.
14. Osteoblastic osteoid (OB-OS), the osteoid surface covered with active osteoblasts per tissue volume.
15. Osteoblastic surface (OB-TS), the osteoblastic surface per parameter of trabecular bone.
16. Osteoblastic index (OBI), the number of osteoblasts per 10 cm bone surface.
17. Active resorption (OCL), the eroded bone surface lined with osteoclasts per parameter of trabecular bone.
18. Inactive resorption (HL), resorptive surface without osteoclasts per parameter of trabecular bone.
19. Osteoclastic index (OCI), number of osteoclasts per 10 cm of trabecular bone surface.
20. Volume of fibrosis (VV-Fib), the area of fibrosis per total tissue volume.

In addition, the following was also calculated:

1. Mineralization front (MFA), the extent of the second fluorescent label divided by the osteoid surface.
2. Mineral apposition rate (MiAR), the mean interlabel distance divided by the interlabel period in days.
3. Total labeled surface (TLS), the extent of the second fluorescent label divided by the trabecular perimeter.
4. Mineralization lag time (MLT), the measure of the time in days during the lifespan of an osteoid moiety when mineralization is not occurring.
5. Bone formation rate surface referent, the volume of mineralized new bone formed per unit area of osteoid surface per unit time.
6. Bone formation rate volume referent, the volume of mineralized new bone made per unit volume of preexisting bone per unit of time.

Bone aluminum content was measured as follows. Samples were washed with a high pressure stream of aluminum-free water until completely devoid of marrow. Specimens were subsequently treated in a muffle furnace at 550° C. for 12–16 hours, the dry weight of each sample was determined, and ashed specimens dissolved in 2 ml of 3% ultrapure nitric acid. After bringing the samples to 10 ml with deionized water, aliquots were assayed for aluminum content in accordance with the procedure of Alderman et al, see *Clin. Chem.*, 26:258–260 (1980).

Statistical analyses. Results are expressed as the mean±SEM. We performed statistical analyses of the data obtained by two-way analysis of variance and the Duncan's multiple range test.

Materials. The authentic 25(OH)D used in the assay for this metabolite was a gift from Dr. Milan Uskokovic, Hoffmann-La Roche Inc., Nutley, NJ [$^3$H]25(OH)D$_3$ (90 CI/mmol) was purchased from Amersham Corp. (Arlington Heights, Ill.). Beagle puppies were obtained from Ridglan Farms (Mount Horeb, Wis.) and normal diets from Teklad (Madison, Wis.).

The results of these experiments are summarized in the following tables.

| | LDA (0.75 mg/kg thrice weekly) | | | | | | IDA (1.00 mg/kg thrice weekly) | | | | | |
|---|---|---|---|---|---|---|---|---|---|---|---|---|
| Dog # (Weight in kg) | 16 (14.6) | 3 (11.6) | 17 (11.8) | 15 (10.9) | 122 (9.8) | X +/− SEM 11.7 ± .796 | 116 (12.2) | 121 (12.3) | 123 (12.9) | 8941 (14.6) | X +/− SEM 13.0 ± .555 | Normal Values |
| | | | | | 8 weeks | | | | | | | |
| BIOCHEMISTRIES | | | | | | | | | | | | |
| Ca ionized (mmol/l) | 1.29 | 1.27 | 1.24 | 1.34 | 1.30 | 1.29 ± 0.17 | 1.35 | 1.35 | 1.30 | 1.10 | 1.29 ± .060 | |
| Ca+ (mg/dl) | 2.34 | 2.28 | 2.38 | 2.41 | 2.41 | 2.36 ± .025 | 2.55 | 2.5 | 2.45 | 2.56 | 2.52 ± .025 | |
| Po4 (mg/dl) | 1.23 | 1.39 | 1.63 | 1.32 | 1.11 | 1.34 ± .087 | 1.38 | 1.31 | 1.20 | 1.43 | 1.33 ± .043 | |
| Alk Po4 (IU) | 58 | 34 | 35 | 22 | | 37.3 ± 7.52 | | | | | | |
| Cr (mg/dl) | .80 | .75 | .72 | .65 | .70 | .724 ± .025 | .90 | .75 | .85 | .82 | .83 ± .031 | |
| iPTH (pg/ml) | 20.87 | 25.85 | 9.25 | 19.29 | 12.65 | 17.58 ± 2.97 | 7.79 | 3.31 | 13.76 | 8.76 | 8.41 ± 2.14 | |
| 25(OH)D | | 65.54 | 74.98 | 55.04 | | 65.2 ± 5.76 | | | | | | |
| 1,25(OH)2D (pg/ml) | 53.67 | 76.7 | 69.4 | 68.8 | | 67.1 ± 4.89 | | | | | | |
| Serum aluminum (ug/l) | 182.3 | 140.9 | 91.13 | 192.4 | 319.6 | 185.3 ± 34.0 | 734.6 | 444.0 | 341.7 | 356.9 | 469.3 ± 91.3 | |
| Woven Osteoid | | | | | | | | | | | | |
| Woven Osteoid Vol (VV-OS-W) % | 0 | 0 | 0 | 0 | 0 | 0 | 0 | .69 | 6.9 | 1.4 | 2.2 ± 1.36 | 0 |
| Woven Osteoid Surface (OS-W) % | 0 | 0 | 0 | 0 | 0 | 0 | 0 | 4.7 | 34.8 | 10.6 | 12.5 ± 6.7 | 0 |
| Relative Woven Osteoid Volume (ROV-W) % | 0 | 0 | 0 | 0 | 0 | 0 | 0 | 2.2 | 15.0 | 4.0 | 5.3 ± 2.9 | 0 |
| Thickness Woven Osteoid (TH-OS-W) um | 0 | 0 | 0 | 0 | 0 | 0 | 0 | 32.4 | 28.8 | 22.4 | 20.9 ± 6.3 | |
| Osteoblasts | | | | | | | | | | | | |
| Surface Density Active Osteoid (SV-OSB) mm2/mm3 | .108 | .069 | .194 | .036 | .163 | 0.014 0.026 | .965 | .147 | .630 | .158 | 0.65 ± 0.16 | 0.344 ± 0.0345 |
| Relative Surface Density of Active Osteoid (SV-OB) mm2/mm3 | .566 | .211 | .284 | .0832 | .585 | 0.346 0.084 | 2.64 | .463 | 1.38 | 2.48 | 1.74 ± 0.4 | 1.26 ± 0.172 |
| Osteoblastic Osteoid (OB/OS) % | 30.2 | 7.0 | 23.8 | 6.2 | 20.5 | 17.5 4.2 | 55.0 | 19.7 | 18.1 | 43.5 | 34.1 ± 7.86 | 40.5 ± 4.11 |
| Osteoblastic Surface (OB/TS) % | 3.5 | 1.33 | 1.80 | 0.7 | 2.8 | 2.03 0.450 | 16.1 | 2.6 | 7.5 | 12.3 | 9.6 ± 2.5 | 6.2 ± 0.45 |
| Osteoblastic Index (OBI) #/10 cm (OBI-W) #/10 cm | 118.3 | 27.8 | 58.8 | 16.4 | 127.4 | 69.7 20.4 | 626.0 | 112.4 | 293.4 (50.0) | 442.7 | 368.6 ± 94.6 | 181.3 ± 23.8 |
| BONE HISTOMORPHOMETRY STATIC PARAMETERS | | | | | | | | | | | | |
| Bone | | | | | | | | | | | | |
| Bone volume (VV) % | 35.8 | 33.5 | 30.8 | 33.4 | 27.9 | 33.3 ± 1.21 | 36.5 | 31.8 | 45.7 | 35.0 | 37.3 ± 2.6 | 27.3 ± 2.3 |
| Surface Density Bone (SV) mm2/mm3 | 5.3 | 5.1 | 4.98 | 5.9 | 5.89 | 5.4 ± 0.173 | 6.01 | 5.66 | 8.44 | 6.96 | 6.8 ± 0.5 | 5.93 ± 0.181 |
| Trabecular Diameter (D-TRAB) um | 354.2 | 316.5 | 327.0 | 287.8 | 241.6 | 305.4 ± 17.1 | 309.3 | 285.7 | 275.8 | 257.6 | 282.1 ± 9.3 | 239.2 ± 12.57 |
| Woven Bone Vol (VV-w) % | 0 | 0 | 0 | 0 | 0 | 0 | 0 | 0 | 0 | 1.0 | 0.25 ± 0.22 | 0 |
| Lamellar osteoid | | | | | | | | | | | | |
| Osteoid Vol (VV-OS) % | 0.63 | 0.69 | 0.52 | 0.62 | 0.60 | 0.612 ± 0.025 | 1.7 | 0.64 | 0.5 | 1.2 | 1.0 ± 0.2 | 0.75 ± .110 |
| Surface Density Osteoid (SV-OS) mm2/mm3 | .588 | .793 | .639 | .723 | .793 | 0.708 ± 0.037 | 1.75 | .482 | .55 | 1.24 | 1.0 ± 0.26 | 0.803 ± 0.0823 |
| Osteoid Surface (OS) % | 12.8 | 15.1 | 9.1 | 10.5 | 13.5 | 12.2 ± 0.958 | 29.2 | 8.5 | 6.5 | 18.0 | 15.6 ± 4.5 | 13.5 ± 1.42 |
| Relative Osteoid Vol (ROV) % | 1.6 | 2.8 | 1.6 | 1.2 | 2.1 | 1.86 ± 0.246 | 4.7 | 2.0 | 1.2 | 3.4 | 2.8 ± 0.67 | 2.4 ± 0.3 |
| Mean Osteoid Seam Width (MOSW) um | 11.3 | 9.7 | 11.0 | 10.3 | 9.2 | 10.3 ± 0.350 | 12.5 | 12.9 | 12.7 | 11.8 | 12.5 ± 0.2 | 9.9 ± 0.81 |
| Resorption | | | | | | | | | | | | |
| Active Resorption (OCL) % | 0.25 | 0.17 | 0.34 | .23 | 1.28 | 0.454 ± 0.186 | .35 | 0 | 0 | 0.09 | 0.09 ± 0.075 | 1.2 ± 0.08 |
| Inactive Resorption (HL) % | 2.52 | 2.35 | 1.21 | 1.10 | 3.64 | 2.16 ± 0.419 | 2.84 | .37 | 1.0 | 6.96 | 1.1 ± 0.546 | 2.8 ± 0.22 |
| Surface Density Active Resorption (SV-OCL) mm2/mm3 | .0173 | .0160 | .0412 | .248 | .0753 | 0.08 ± 0.039 | .0213 | 0 | 0 | 0.005 | 0.005 ± 0.005 | 0.092 ± 0.0179 |
| Depth of Resorption (D-LAC) um | 12.62 | 11.2 | 12.5 | 9.0 | 10.5 | 11.2 ± 0.60 | 15.2 | 15.5 | 16.0 | 11.7 | 11.7 ± 3.37 | 12.1 ± 0.892 |
| Osteoclastic Index (OCI) #/10cm | 11.6 | 7.2 | 14.4 | 7.6 | 28.8 | 13.9 ± 3.53 | 7.1 | 0 | 0 | 1.78 | 1.78 ± 1.54 | 32.3 ± 2.37 |
| Corrected Active Resorption (OCL-R) % | .30 | .184 | 0.37 | 0.25 | 1.5 | 0.52 ± 0.221 | .50 | 0 | 0 | 0.125 | 0.125 ± 0.10 | 1.32 ± 0.09 |
| Fibrosis | | | | | | | | | | | | |

-continued

| | LDA (0.75 mg/kg thrice weekly) | | | | X +/− SEM | IDA (1.00 mg/kg thrice weekly) | | | | X +/− SEM | Normal Values |
|---|---|---|---|---|---|---|---|---|---|---|---|
| Dog # (Weight in kg) | 16 (14.6) | 3 (11.6) | 17 (11.8) | 15 (10.9) | 122 (9.8) | 11.7 ± .796 | 116 (12.2) | 121 (12.3) | 123 (12.9) | 8941 (14.6) | 13.0 ± .555 | |
| Volume Fibrosis (VV-Fib) % | 0 | 0 | 0 | 0 | 0 | 0 | .37 | 5.6 | 19 | .01 | 6.2 ± 3.84 | 0 |
| Fibrosis Marrow (Fib-M) % | 0 | 0 | 0 | 0 | 0 | 0 | .59 | 8.3 | 34.8 | .015 | 10.9 ± 7.1 | 0 |
| BONE HISTOMORPHOMETRY DYNAMIC PARAMETERS | | | | | | | | | | | | |
| Mineralization | | | | | | | | | | | | |
| Mineralization Front (MFA) % | 73.1 | 49.1 | 40.2 | 51.3 | 46.0 | 51.9 ± 5.02 | 26.4 | 20.6 | 4.1 | 5.6 | 14.2 ± 4.8 | 69.9 ± 4.19 |
| Mineralization Apportion Rate (um/d) | 0.70 | 0.77 | 0.87 | 0.53 | 1.26 | 0.83 ± 0.109 | .981 | 1.326 | .800 | .801 | 0.98 ± 0.12 | 0.76 ± 0.060 |
| Total Labeled Surface (TLS) % | 9.1 | 5.6 | 4.7 | 4.4 | 4.9 | 5.7 ± 0.76 | 6.1 | 2.2 | 1.3 | 1.6 | 2.8 ± 0.97 | 8.9 ± 1.10 |
| Mineralization Lag Time (MLT) d | 18.1 | 13.5 | 12.0 | 19.6 | 7.3 | 14.1 ± 1.97 | 12.74 | 9.73 | 15.87 | 14.75 | 13.3 ± 1.16 | 18.0 ± 1.74 |
| Formation | | | | | | | | | | | | |
| Bone Formation Surface (BF) mm3/mm2-yr | 0.0232 | 0.0157 | 0.0149 | 0.0086 | 0.0225 | 0.0170 ± .00241 | .0218 | .0106 | .0038 | .0047 | 0.010 ± 0.004 | 0.241 ± 0.0025 |
| Bone Formation Volume (BF) mm3/mm3-yr | 0.122 | 0.078 | 0.076 | 0.051 | 0.133 | 0.0918 ± 0.0137 | .1313 | .0602 | .0320 | .0326 | 0.064 ± 0.020 | 0.1444 ± 0.0606 |
| Aluminum | | | | | | | | | | | | |
| Aluminum Surface (Als/TS) % | 16.3 | 11.3 | 4.7 | 4.8 | 7.3 | 8.9 ± 1.98 | | | | 13.9 | | |
| Bone Aluminum (BAC) ug/g | 55.6 | 59.5 | 59.6 | 96.5 | 57.9 | 67.8 ± 9.6 | 65.8 | 118.1 | 144.3 | 66.4 | 98.6 ± 16.93 | |

16 WEEKS

| Dog # (Weight in kg) | 16(16.0) | 3(13.0) | LDA (0.75 mg/kg thrice weekly) 17(12.7) | 15(11.5) | 122(10.2) | X +/− SEM 11.7 .796 | 116(11.5) | 121(10.3) | IDA (1.00 mg/kg thrice weekly) 123(12.3) | 894(13.9) | X +/− SEM 12.0 .755 | Normal values |
|---|---|---|---|---|---|---|---|---|---|---|---|---|
| BIOCHEMISTRIES | | | | | | | | | | | | |
| Ca ionized (mmol/l) | 1.30 | 1.23 | 1.30 | 1.29 | 1.26 | 1.28 ± 0.14 | 1.29 | 1.30 | 1.28 | 1.31 | 1.295 ± .0065 | |
| Ca+ (mg/dl) | 2.50 | 2.42 | 2.38 | 2.49 | 2.15 | 2.39 ± .064 | 2.21 | 2.24 | 2.26 | 2.35 | 2.265 ± .030 | |
| Po4 (mg/dl) | 1.25 | 1.63 | .93 | 1.31 | .903 | 1.20 ± .134 | .93 | .863 | .951 | 1.21 | 1.0 ± .066 | |
| Alk Po4 (IU) | 29 | 37 | 15 | 18 | | 24.75 ± 5.07 | | | | | | |
| Cr (mg/dl) | .72 | .69 | .66 | .62 | .70 | .678 ± .017 | .95 | 1.05 | 1.0 | .88 | .97 ± .036 | |
| iPTH (pg/ml) | 13.65 | 28.03 | 18.05 | 15.85 | 31.92 | 21.5 ± 3.58 | 16.39 | 11.91 | 13.90 | 22.2 | 16.1 ± 2.23 | |
| 25(OH)D | | | | | | | | | | | | |
| 1,25(OH)2D (pg/ml) | 68.5 | 74.13 | 101.5 | 65.7 | | 77.5 ± 7.1 | | | | | | |
| Serum aluminum (ug/l) | | | | | | | | | | | | |

| Dog # (Weight in kg) | 16(14.6) | 3(11.6) | LDA (0.75 mg/kg thrice weekly) 17(11.8) | 15(10.9) | 122(9.8) | X +/− SEM 11.7 .796 | 116(12.2) | 121(12.3) | IDA (1.00 mg/kg thrice weekly) 123(12.9) | 894(14.6) | X +/− SEM 13.0 .555 | Normal values |
|---|---|---|---|---|---|---|---|---|---|---|---|---|
| BONE HISTOMORPHOMETRY STATIC PARAMETERS | | | | | | | | | | | | |
| Bone | | | | | | | | | | | | |
| Bone volume (VV) % | 34.3 | 40.8 | 57.9 | 32.9 | 28.6 | 38.9 ± 4.60 | 39.9 | 46.1 | 60.8 | 54.6 | 50.4 ± 4.0 | |
| Surface Density Bone (SV) mm2/mm3 | 8.3 | 7.7 | 7.1 | 6.93 | 5.52 | 7.1 ± 0.42 | 5.64 | 7.03 | 8.47 | 10.18 | 7.8 ± 0.8 | |
| Trabecular Diameter (D-TRAB) um | 322.0 | 270.0 | 246.5 | 241.8 | 263.9 | 268.8 ± 12.78 | 360.6 | 333.6 | 365.5 | 272.9 | 333.2 ± 18.4 | |
| Woven Bone Vol (VV-w) % | 0 | 0 | 0 | 0 | 0 | 0 | 0.8 | 4.5 | 5.7 | 4.0 | 38 ± 0.91 | |
| Lamellar Osteoid | | | | | | | | | | | | |
| Osteoid Vol (VV-OS) % | 2.70 | .91 | 1.20 | 1.30 | 0.90 | 1.4 ± 0.30 | 3.0 | 1.93 | 2.49 | 2.86 | 2.6 ± 0.2 | |
| Surface Density Osteoid (SV-OS) mm2/mm3 | 1.809 | 1.167 | 1.321 | 1.370 | .884 | 1.31 ± 0.135 | 2.157 | 1.853 | 1.85 | 3.42 | 2.3 ± 0.3 | |
| Osteoid Surface (OS) % | 26.8 | 13.6 | 15.2 | 23.0 | 16.0 | 18.9 ± 2.28 | 38.3 | 26.4 | 21.9 | 33.6 | 30.1 ± 3.2 | |
| Relative Osteoid Vol (ROV) % | 4.8 | 2.3 | 3.6 | 4.7 | 3.0 | 3.68 ± 0.432 | 7.53 | 4.2 | 4.1 | 5.2 | 5.3 ± 0.09 | |
| Mean Osteoid Seam Width (MOSW) um | 15.1 | 11.2 | 13.5 | 11.8 | 11.5 | 12.6 ± 0.660 | 16.7 | 12.7 | 16.9 | 10.4 | 14.2 ± 1.4 | |
| Woven Osteoid | | | | | | | | | | | | |
| Woven Osteoid Vol (VV-OS-W) % | 0 | 0 | 0 | 0 | 0 | 0 | .992 | 1.4 | 1.1 | .23 | 0.9 ± 0.22 | |
| Woven Osteoid Surface (OS-W) % | 0 | 0 | 0 | 0 | 0 | 0 | 5.95 | 8.64 | 7.1 | 1.6 | 5.8 ± 1.3 | |
| Relative Woven Osteoid Volume (ROV-W) % | 0 | 0 | 0 | 0 | 0 | 0 | 2.49 | 5.0 | 1.8 | .412 | 2.4 ± 0.83 | |
| Thickness Woven Osteoid (TH-OS-W) um | 0 | 0 | 0 | 0 | 0 | 0 | 35.6 | 28.8 | 24.1 | 14.3 | 25.7 ± 3.9 | |
| Osteoblasts | | | | | | | | | | | | |
| Surface Density Active Osteoid (SV-OSB) mm2/mm3 | .3734 | .2281 | .5628 | .2378 | .174 | 0.315 ± 0.063 | .366 | .242 | .867 | .418 | 0.47 ± 0.12 | |

-continued

| | | | | | 16 WEEKS | | | | | |
|---|---|---|---|---|---|---|---|---|---|---|
| Relative Surface Density of Active Osteoid (SV-OB) mm2/mm3 | .9463 | .560 | 1.159 | .712 | .608 | 0.797 ± 0.100 | .918 | .525 | 1.43 | .766 | 0.9 ± 0.17 |
| Osteoblastic Osteoid (OB/OS) % | 24.6 | 25.1 | 36.8 | 18.2 | 19.7 | 24.9 ± 2.923 | 14.7 | 9.82 | 35.4 | 11.7 | 17.9 ± 5.12 |
| Osteoblastic Surface (OB/TS) % | 6.7 | 3.0 | 5.6 | 3.4 | 3.2 | 4.4 ± 0.67 | 6.5 | 3.4 | 10.2 | 4.1 | 6.1 ± 1.3 |
| Osteoblastic Index (OBI) #/10 cm | 275 | 108 | 232 | 130 | 125.7 | 174.1 ± 29.8 | 265.9 | 156.9 | 470.9 | 159.8 | 263.3 ± 63.8 |
| (OBI-W) #/10 cm | | | | | | | | | (50.0) | | |
| Resorption | | | | | | | | | | | |
| Active Resorption (OCL) % | 1.74 | 0.80 | 1.75 | .40 | 0.86 | 1.11 ± 0.242 | 0 | 0 | .14 | 0 | 0.035 ± 0.003 |
| Inactive Resorption (HL) % | 3.46 | 1.82 | 3.51 | 1.31 | 1.40 | 2.3 ± 0.440 | .67 | .84 | .57 | 0 | 0.52 ± 0.158 |
| Surface Density Active Resorption(SV-OCL) mm2/mm3 | 0.0814 | 0.0954 | 0.1238 | 0.054 | 0.0474 | 0.08 ± 0.0125 | 0 | 0 | .0122 | 0 | 0.03 ± 0.0264 |
| Depth of Resorption (D-LAC) um | 14.3 | 13.5 | 12.7 | 12.4 | 11.3 | 12.8 ± 0.45 | 10.6 | 11.3 | 18.8 | 0 | 10.2 ± 3.35 |
| Osteoclastic Index (OCI) #/10 cm | 24.0 | 27.3 | 39.3 | 20.7 | 20.5 | 26.4 ± 3.1 | 0 | 0 | 1.5 | 0 | 0.375 ± 0.325 |
| Corrected Active Resorption (OCL-R) % | 2.21 | .91 | 2.0 | .44 | 1.02 | 1.333 ± 0.300 | 0 | 0 | .20 | 0 | 0.05 ± 0.043 |
| Fibrosis | | | | | | | | | | | |
| Volume Fibrosis (VV-Fib) % | 1.1 | 0.55 | 0 | .03 | 0 | 0.34 ± 0.195 | 11.5 | 37.8 | 11.9 | 2.46 | 15.9 ± 6.6 |
| Fibrosis Marrow (Fib-M) % | 0.91 | 2.21 | 0 | .04 | 0 | 0.632 ± 0.386 | 19.2 | 70.2 | 30.3 | 5.4 | 31.3 ± 12.1 |
| BONE HISTOMORPHOMETRY DYNAMIC PARAMETERS | | | | | | | | | | | |
| Mineralization | | | | | | | | | | | |
| Mineralization Front (MFA) % | 42.0 | 49.5 | 54.2 | 31.3 | 52.9 | 46.0 ± 3.79 | 11.9 | 10.3 | 32.7 | 3.6 | 14.63 ± 5.45 |
| Mineralization Apposition Rate (um/d) | 1.58 | 0.73 | 0.76 | 0.84 | .954 | 0.973 ± 0.140 | .625 | 1.057 | 1.324 | 1.09 | 1.03 ± 0.124 |
| Total Labeled Surface (TLS) % | 9.6 | 5.2 | 6.5 | 5.7 | 6.6 | 6.72 ± 0.689 | 4.1 | 2.8 | 7.5 | 1.0 | 3.9 ± 1.19 |
| Mineralization Lag Time (MLT) d | 9.5 | 16.7 | 17.8 | 16.1 | 12.0 | 14.4 ± 1.41 | 26.3 | 12.02 | 12.8 | 9.54 | 15.2 ± 3.28 |
| Formation | | | | | | | | | | | |
| Bone Formation Surface (BF) mm3/mm2-yr | 0.056 | 0.0138 | 0.0180 | 0.0175 | 0.0230 | 0.026 ± 0.007 | .0114 | .0108 | .0362 | .0040 | 0.0016 ± 0.006 |
| Bone Formation Volume (BF) mm3/mm3-yr | 0.465 | 0.1005 | 0.1280 | 0.1213 | 0.127 | 0.1884 ± 0.062 | .0460 | .0760 | .307 | .0405 | 0.122 ± 0.054 |
| Aluminum | | | | | | | | | | | |
| Aluminum Surface(Als/TS) % | 133.9 | 22.4 | 21.8 | 30.5 | | 24.9 ± 2.29 | | | | | |
| Bone Aluminum (BAC) ug/g | | 163.2 | 223.7 | 204.6 | | 181.4 ± 17.5 | | | | | |

| | | | | | | Normal values |
|---|---|---|---|---|---|---|
| Dog # (Weight in kg) | 5(10.0) | 18(12.6) | 14(12.1) | 20(11.5) | X +/− SEM 11.55 ± .563 | |

HDA
(1.25 mg/kg thrice weekly)

BONE HISTOMORPHOMETRY

-continued

| STATIC PARAMETERS | 16 WEEKS | | | | |
|---|---|---|---|---|---|
| Bone | | | | | |
| Bone volume (VV) % | 32.7 | 45.7 | 38.5 | 26.3 | 35.8 ± 3.6 | 27.3 ± 2.3 |
| Surface Density Bone (SV) mm2/mm3 | 6.6 | 8.2 | 6.6 | 6.3 | 6.9 ± 0.4 | 5.93 ± 0.181 |
| Trabecular Diameter (D-TRAB) um | 254.2 | 285.1 | 312.1 | 228.5 | 270 ± 15.8 | 239.2 ± 12.57 |
| Woven Bone Vol (VV-w) % | 0 | 0 | 1.6 | 1.0 | | 0 |
| Lamellar Osteoid | | | | | | |
| Osteoid Vol (VV-OS) % | 1.2 | .50 | 3.0 | .23 | 1.2 ± 0.54 | 0.75 ± .110 |
| Surface Density Osteoid (SV-OS) mm2/mm3 | 1.02 | .290 | 2.47 | .576 | 1.1 ± 0.42 | 0.803 ± 0.0823 |
| Osteoid Surface (OS) % | 15.7 | 3.61 | 39.6 | 5.3 | 16.1 ± 7.2 | 13.5 ± 1.42 |
| Relative Osteoid Vol (ROV) % | 3.4 | .90 | 7.62 | 7.9 | 3.1 ± 1.4 | 2.4 ± 0.3 |
| Mean Osteoid Seam Width (MOSW) um | 12.7 | 16.9 | 13.8 | 8.5 | 13.0 ± 1.5 | 9.9 ± 0.81 |
| Woven Osteoid | | | | | | |
| Woven Osteoid Vol (VV-OS-W) % | 7.7 | 16.4 | 1.2 | 2.0 | 6.83 ± 3.03 | 0 |
| Woven Osteoid Surface (OS-W) % | 42.8 | 60.6 | 8.2 | 9.6 | 30.3 ± 11.2 | 0 |
| Relative Woven Osteoid Volume (ROV-W) % | 23.3 | 37.2 | 3.2 | 7.3 | 17.8 ± 6.75 | 0 |
| Thickness Woven Osteoid (TH-OS-W) um | 33.5 | 39.9 | 28.9 | 35.2 | 34.4 ± 1.97 | 0 |
| Osteoblasts | | | | | | |
| Surface Density Active Osteoid (SV-OSB) mm2/mm3 | .339 | .208 | .417 | .105 | 0.267 ± 0.06 | 0.344 ± 0.0345 |
| Relative Surface Density of Active Osteoid (SV-OB) mm2/mm3 | 1.04 | .444 | .710 | .420 | 0.65 ± 0.13 | 1.26 ± 0.172 |
| Osteoblastic Osteoid (OB/OS) % | 9.1 | 4.0 | 14.1 | 15.7 | 8.1 ± 2.0 | 40.5 ± 4.11 |
| Osteoblastic Surface (OB/TS) % | 5.2 | 4.3 | 7.1 | 1.6 | 4.6 ± 0.99 | 6.2 ± 0.45 |
| Osteoblastic Index (OBI) #/10 cm | 170.0 | 74.8 | 214.4 | 53.3 | 12 | 181.3 ± 23.8 |
| (OBI-W) #/10 cm | (1243.0) | (1374.0) | (286.0) | (300.0) | (800.8 ± 254.9) | |
| Total Osteoblastic Index (OBI) | 1413.0 | 1448.8 | 500.4 | 353.3 | 928.9 ± 252.4 | 181.3 ± 23.8 |
| Resorption | | | | | | |
| Active Resorption (OCL) % | 0 | .14 | 0 | 0.185 | 0.08 ± 0.041 | 1.2 ± 0.08 |
| Inactive Resorption (HL) % | 0.32 | 0.52 | 0.5 | 2.3 | 0.91 ± 0.403 | 2.8 ± 0.22 |
| Surface Density Active Resorption (SV-OCL) mm2/mm3 | 0 | .025 | 0 | .004 | 0.01 ± 0.01 | 0.092 ± 0.0179 |
| Depth of Resorption (D-LAC) um | 6.62 | 17.8 | 7.8 | 11.3 | 10.9 ± 2.18 | 12.1 ± 0.892 |
| Osteoclastic Index | 0 | 4.8 | 0 | 2.2 | 1.8 ± 0.99 | 32.3 ± 2.377 |

-continued

| | 16 WEEKS | | | |
|---|---|---|---|---|
| (OCl) #/10 cm | | | | |
| Corrected Active Resorption (OCL-R) % | 0 | .66 | 0 | .087 | 0.187 ± 0.138 | 1.32 ± 0.09 |
| Fibrosis | | | | |
| Volume Fibrosis (VV-Fib) % | 44.7 | 28.2 | .05 | 55.7 | 32.2 ± 10.4 | 0 |
| Fibrosis Marrow (Fib-M) % | 66.8 | 53.1 | .09 | 76.6 | 49.1 ± 14.8 | 0 |
| BONE HISTOMORPHOMETRY DYNAMIC PARAMETERS | | | | |
| Mineralization | | | | |
| Mineralization Front (MFA) % | 15.3 | 9.6 | 46.3 | 24.6 | 23.95 ± 6.99 | 69.9 ± 4.19 |
| Mineralization Apposition Rate (um/d) | | 1.1 | 0.67 | 1.0 | 0.69 ± 0.22 | 0.76 ± 0.060 |
| Total Labeled Surface (TLS) % | 8.2 | 4.4 | 14.7 | 3.6 | 7.73 ± 4.39 | 8.9 ± 1.10 |
| Mineralization Lag Time (MLT) d | | | | | | 18.0 ± 1.74 |
| Formation | | | | |
| Bone Formation Surface (BF) mm3/mm2-yr | 0 | .0176 | .036 | .0131 | 0.017 ± 0.0064 | 0.241 ± 0.0025 |
| Bone Formation Volume (BF) mm3/mm3-yr | 0 | .1449 | .237 | .0827 | 0.116 ± 0.043 | 0.1444 ± 0.0606 |
| Aluminum | | | | |
| Aluminum Surface (Als/TS) % | 32.8 | 28.4 | 22.6 | 22.4 | 26.6 ± 2.17 | 0 |
| Bone Aluminum (BAC) ug/g | 141.3 | 134.6 | 192.2 | 139.4 | 151.9 ± 11.7 | 2.3 ± 0.74 |

Considering first the data obtained after 8 weeks of administration of low- and intermediate-dose aluminum in doses noted in the tables, the biochemistries reported clearly demonstrate that administration of aluminum does not alter the serum calcium or phosphorus concentration. In addition, renal function, as assessed by measurement of serum creatinine, is not impaired. In contrast, administration of the aluminum results in an apparent dose-dependent increase in the serum aluminum concentration. In accord with the increased serum aluminum, a discernable pattern of changes in bone histomorophometry is observed. First and perhaps most importantly, the bone volume is substantially increased in both low- and intermediate-dose treated animals. This difference is particularly notable in the intermediate-dosed animals. Notably, these changes occur in accord with a marked increase in the trabecular diameter. The changes in the intermediate-dosed animals are particularly notable when further data are observed. Thus, a fair degree of woven osteoid is observed in the treated animals in spite of the absence of this form of bone in the controls. The woven osteoid is a signal of increased osteoblast activity and is appropriately mirrored by a tremendous increase in the osteoblasts as expressed by a number of measurements, including an osteoblastic surface and an osteoblastic index. Commensurate with the change in osteoblast number and function, the amount of bone resorption is markedly decreased in the aluminum-treated animals. The changes in bone histomorophometry are accompanied by the presence of aluminum on the bone surface and in the bone as reflected by these measurements.

Next, considering the data at 16 weeks of therapy, it can be seen that the results therefrom are even more impressive. Observations at this time include not only low- and intermediate-dose treatment but high dosage treatments as well. The biochemistries at 16 weeks of therapy are similar to those obtained at 8 weeks. However, the bone histomorophometry is particularly revealing. In particular, it is noted that the bone volume, including the mineralized bone volume (V), the osteoid volume and the woven osteoid volume are markedly increased. This is again an index of increased bone formation. Indeed, the surface density of bone is accordingly increased as is the trabecular diameter where mineralized bone prevails. Again, woven osteoid occurring at the intermediate- and high-dosed animals signals increase osteoblastic activity which is again reflected by the osteoblast number. The low-dosed treated animals, while manifesting increased bone volume, do not have excess woven osteoid but manifest an increase in osteoblasts compared to their 8-week controls. It should also be noted that cessation of aluminum results in complete mineralization of the bone formed a priori and ultimate remodeling to lamellar bone.

Thus, in accordance with the present invention, a method is now provided for stimulating the formation of new mammalian bone in such a manner that the bone formation appears to be uncoupled from the normally linked process of bone resorption. This method and the compositions disclosed therefor can thus be used quite advantageously in the treatment of human bone diseases, particularly those characterized by osteopenia.

Having now fully described the present invention, it will be apparent to one of ordinary skill in the art that many changes and modifications can be made thereto without departing from the spirit or scope of the invention as set forth herein.

What is claimed and desired to be secured by Letters Patent of the U.S. is:

1. A liquid pharmaceutical composition for stimulating the formation of new mammalian bone, which comprises an effective amount of one or more water-soluble aluminum salts and water for injection, wherein said water-soluble aluminum salt is selected from the group consisting of aluminum acetate, aluminum bromate, aluminum chlorate, aluminum citrate, aluminum sulfate, aluminum lactate, and aluminum nitrate; said liquid composition having a concentration of said aluminum salt therein of about 0.1 to 20% by weight.

2. The liquid pharmaceutical composition according to claim 1, wherein said water-soluble aluminum salt is aluminum nitrate, aluminum sulfate, aluminum citrate and aluminum lactate.

3. The liquid pharmaceutical composition according to claim 1, which has a concentration of 0.5% by weight of aluminum salt therein.

4. The liquid pharmaceutical composition according to claim 1, which is in unit dosage form and contains from about 10 to 500 mg of said water-soluble aluminum salt.

5. A method for simulating the formation of new bone in a mammal in need thereof, which entails administering an effective amount of one or more water-soluble aluminum salts to a mammal, wherein said water-soluble aluminum salt is selected from the group consisting of aluminum acetate, aluminum bromate, aluminum chlorate, aluminum citrate, aluminum sulfate, aluminum lactate and aluminum nitrate.

6. The method according to claim 5, wherein said mammal is a human.

7. The method according to claim 5, wherein said water-soluble aluminum salts are in the form of a liquid pharmaceutical composition, comprising an effective amount of said one or more of said water-soluble aluminum salts, the liquid composition having a concentration of said aluminum salt therein of about 0.1 to 20% by weight; and said composition is administered intravenously.

8. The method according to claim 5, wherein said water-soluble aluminum salts are in the form of a solid pharmaceutical composition in unit dosage form selected from the group consisting of tablets, candies and chewable gums; which comprises, as an active ingredient, from about 10 to 500 mg of said one or more of said water-soluble aluminum salts and a pharmaceutically acceptable carrier; and said composition is administered orally.

* * * * *